United States Patent [19]

Power

[11] Patent Number: 5,524,615
[45] Date of Patent: Jun. 11, 1996

[54] VENTILATOR AIRWAY FLUID COLLECTION SYSTEM

[75] Inventor: John S. Power, Galway, Ireland

[73] Assignee: Puritan-Bennett Corporation, Overland Park, Kans.

[21] Appl. No.: 303,054

[22] Filed: Sep. 8, 1994

[51] Int. Cl.⁶ .............................. A62B 31/00; A62B 7/00
[52] U.S. Cl. ................. 128/205.12; 128/205.27; 128/206.22; 128/201.28
[58] Field of Search .................. 128/207.14, 205.12, 128/206.22, 911, 912, 207.16, 201.28, DIG. 24, 205.27, 205.24; 251/149.9; 604/248, 905

[56] References Cited

U.S. PATENT DOCUMENTS

| | | | |
|---|---|---|---|
| 4,327,718 | 5/1982 | Cronenberg | 128/205.12 |
| 4,457,305 | 7/1984 | Shanks et al. | 128/205.12 |
| 4,576,199 | 3/1986 | Svensson et al. | 251/149.5 |
| 5,168,868 | 12/1992 | Hicks | 128/205.12 |

FOREIGN PATENT DOCUMENTS 1456570  11/1976  United Kingdom.

*Primary Examiner*—Ren Yan
*Assistant Examiner*—V. Srivastava
*Attorney, Agent, or Firm*—Fulwider Patton Lee & Utecht

[57] ABSTRACT

The ventilator airway fluid collection system permits the maintenance of PEEP in a patient breathing circuit when a fluid collector vial is removed. A fluid collection vial is connected to the airway from which fluid is to be collected by connection to an arm of a tee connector, and a disc assembly is provided in the arm of the tee connector that closes the opening to the vial when the vial is removed. The disc assembly includes a first disc fixedly mounted in the connector arm, and a second disc rotatably mounted to the first disc. The first disc includes at least one aperture, and the second disc includes at least one corresponding aperture. The second, rotatable disc includes at least one tab for indexing the second disc's aperture to open the passageway to the vial when the vial is attached, and to close the passageway when the vial is removed.

7 Claims, 1 Drawing Sheet

VENTILATOR AIRWAY FLUID COLLECTION SYSTEM

BACKGROUND OF THE INVENTION

1. Field of the Invention

This invention relates generally to breathing ventilators, and more particularly concerns a ventilator airway fluid collection system including a fluid collector vial that is connected to an airway of the ventilator, and which allows PEEP to be maintained in a patient breathing circuit when the fluid collector vial is removed for emptying.

2. Description of Related Art

Breathing ventilator systems conventionally provide a breathing gas at elevated pressure levels. Pressure support is also known in the art by other names, e.g. inspiratory assist, pressure assist, or inspiratory pressure assist. Pressure in a ventilator airway is commonly maintained at PEEP (Patient End Expiratory Pressure, a baseline pressure value) to assist patient breathing efforts. Breathing gas is also often supplemented with a higher proportion of oxygen than is found in the ambient atmosphere, and is commonly humidified. Consequently, moisture regularly condenses in a ventilator airway, and one or more fluid collector vials can be placed in strategic locations in the airway to collect such fluid condensate.

A common problem with such fluid collection systems is that PEEP can be lost to the patient when the airway is opened to atmospheric pressure when such collector vials are removed to dispose of collected fluid. Fluid can also be sprayed out of the airway if the ventilator is operating when the fluid collection vial is removed, which can be unpleasant and unhygienic.

One known solution to this problem has been to provide spring loaded seals which close off the fluid collection opening in the airway when a collection vial is removed. However, such spring loaded seals can be expensive, difficult to clean, and can fail due to blockage of the seal, cracking of the seal, failure of the spring, and similar problems.

It is therefore desirable to provide a ventilator airway fluid collection system that is less complex and less expensive, more robust and reliable than such spring loaded seal systems, that will allow PEEP to be maintained in a patient breathing circuit when a fluid collector vial is removed for emptying. It would also be desirable to provide such a ventilator airway fluid collection system that can readily be substituted for existing fluid collection systems. The present invention meets these needs.

SUMMARY OF THE INVENTION

Briefly, and in general terms, the present invention provides for a ventilator airway fluid collection system that permits the maintenance of PEEP in a patient breathing circuit when a fluid collector vial is removed.

The present invention accordingly provides for a ventilator airway fluid collection system for collecting fluid from a ventilator airway comprising fluid container means for receiving and containing fluid from the ventilator airway, and connector means for connecting the fluid container means in sealed fluid communication with the ventilator airway. The connector means has a passageway adapted to be connected in fluid communication with the opening of the fluid container means, and coupling means are provided on the container means for coupling the container means to the connector means.

Closure means are disposed between the connector passageway and the opening of the fluid container for opening and closing fluid communication between the connector passageway and the opening of the fluid container. The closure means advantageously includes indexing means for switching the closure means between an open position when the fluid container means is coupled to the connector means allowing fluid communication between the connector fluid passageway and the opening of the fluid container, and a closed position when the container means is removed from the connector means, preventing fluid communication between the connector fluid passageway and the atmosphere.

In a presently preferred embodiment, the closure means comprises a disc assembly including a first disc fixedly mounted between the connector fluid passageway and the opening of the fluid container means and a second disc rotatably mounted to the first disc, the first disc having at least one aperture defined therein, and the second disc having at least one corresponding aperture defined therein. The indexing means also currently preferably comprises at least one tab disposed on the second, rotatable disc, and at least one corresponding locating stop on the mouth of the fluid container means. The second disc can thus be rotated to the open position by rotation of the fluid container to align the second disc aperture with the first disc aperture to allow fluid communication between the connector means and the fluid container means. The second disc can also be rotated to the closed position by rotation of the fluid container to bring the first disc aperture and second disc aperture out of alignment.

These and other aspects and advantages of the invention will become apparent from the following detailed description, and the accompanying drawings, which illustrate by way of example the features of the invention.

DETAILED DESCRIPTION OF A PREFERRED EMBODIMENT

Figure 1:
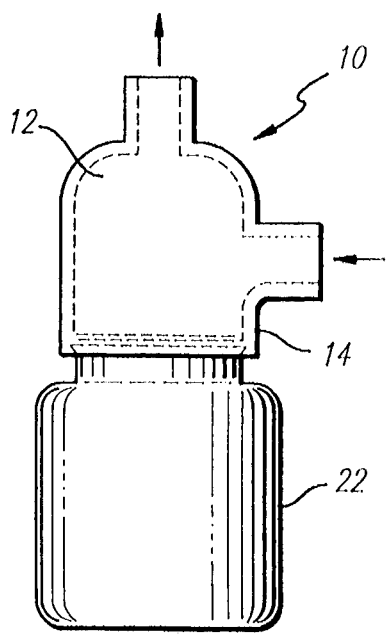
FIG. 1 is an elevational view of the ventilator airway fluid collection system of the invention.

Ventilator airway fluid collection systems in which a fluid collection vial must be disconnected in order to empty the vial can interrupt the maintenance of PEEP, if the airway is opened to the atmosphere, or if the ventilator is turned off for emptying the vial. Fluid can also be sprayed out of the airway if the ventilator is on when the fluid collection vial is removed. While spring loaded seals can be used to close off the fluid collection opening in the airway, such seals can be expensive, and difficult to clean and maintain.

As is illustrated in the drawings, the invention is accordingly embodied in a ventilator airway fluid collection system 10 including connector means for connecting the fluid container means in sealed fluid communication with the ventilator airway, such as a three-way or tee connector 12, typically made of silicone, that is attached to a ventilator airway line (not shown), with exhaled air or breathing gas being received in one port from a patient and exiting through another port to an exhalation module (not shown). The tee connection preferably has a bell shape to provide a relatively large area to allow for a pressure drop, to improve the flow of liquid to the vial.

A fluid collection port 14 of the tee connector has a mouth opening 15 with a surface defining two key slots 16 and an inner radial groove 18 for receiving and mating with two corresponding mounting flanges or tabs 20 of a fluid container means for containing fluid from the ventilator airway such as fluid collection vial 22, providing a bayonet fitting for removably coupling the vial to the connector. The radial groove serves to prevent removal of the vial unless the mounting flanges or tabs 20 on the vial are correctly oriented, so that the aperture between the patient circuit and the vial is closed off when the vial is removed.

Other similar coupling means for coupling the vial to the connector consisting of similar key slots or apertures and corresponding bayonet tabs may also be suitable, such as locking tabs and slots arranged 90° apart, or with tabs or pins extending from the mouth of the connector port for the vial to mate with slots in the mouth of the vial, or the like. The fluid collection vial has a mouth defining an opening 23 through which fluid enters the vial, and which is removably connected to the fluid collection port. The fluid collection port for the vial also preferably includes another inner radial groove 24 in which a first, non-rotatable or fixed disc 26 is mounted.

In a preferred embodiment, the fixed disc is made of stainless steel or a similar non-corrosive material, and includes a semicircular or 180° aperture 28. A second, smaller rotatable disc 30, also preferably made of stainless steel, and having a corresponding semicircular or 180° aperture 32, is preferably rotatably secured to the fixed disc by a pivot pin 34 extending through the centers of the discs. While 180° apertures in each disc are currently preferred, other sizes, shapes, and numbers of openings can be suitable, such as corresponding sets of a plurality of smaller holes or quadrants in each disc, and the like. The disc assembly forms a closure means for opening and closing fluid communication between the connector fluid passageway and the mouth of the tee connector and the opening of the fluid collection vial. The discs are preferably in immediate contact with one another, so that when the apertures are out of alignment in a closed position, fluid communication between the connector fluid passageway and the mouth of the tee connector is blocked.

Figure 2:
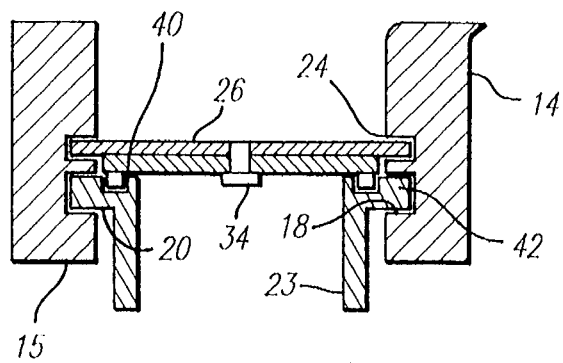
FIG. 2 is an enlarged cross-sectional view of the union between the connector and fluid collector vial of the ventilator fluid collection system.
Figure 3:
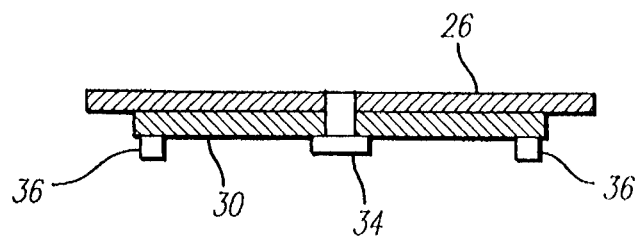
FIG. 3 is a side elevational view of the closure disc assembly of the ventilator fluid collection system.
Figure 4:
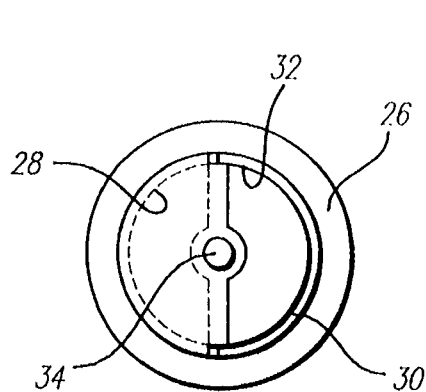
FIG. 4 is a plan view of the closure disc assembly of FIG. 3.
Figure 5:
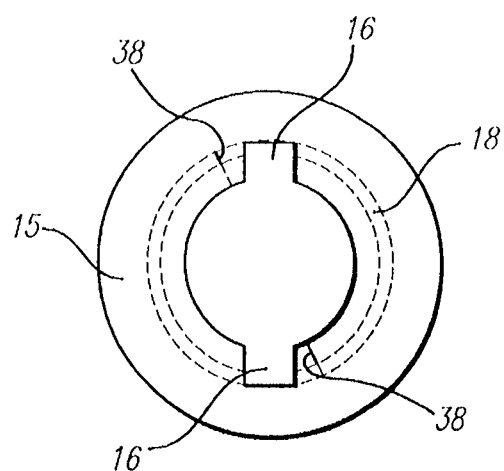
FIG. 5 is a bottom plan view of the fluid collection port of the tee connector of the ventilator fluid collection system.

As is shown in FIGS. 2–4, the second, rotatable disc preferably includes two indexing tabs 36 that cooperate with two corresponding locating stops 38 in a groove 40 in the neck flange 42 of the vial 22. At least one such indexing tab is provided on the rotatable disc, to provide an indexing means for switching the closure means between an open position when the fluid container means is coupled to the connector means to allow fluid communication between the connector fluid passageway and the opening of the fluid container, and a closed position when the container means is removed from the connector means, preventing fluid communication between the connector fluid passageway and the atmosphere. When the vial is attached to the fluid collection port of the connector, and the vial is rotated to lock the vial into position, the rotatable disc is correspondingly rotated to the open position, thereby opening the passageway through the fluid collection port into the vial, to permit liquid to enter the vial from the airway. Similarly, the passageway through the fluid collection port is closed when the vial is rotated for detachment of the vial, to allow PEEP to be maintained in the ventilator airway.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A ventilator airway fluid collection system for collecting fluid from a ventilator airway, comprising:

a fluid container for containing fluid from the ventilator airway, the fluid container having an opening through which fluid is received from the ventilator airway;

connector means for connecting the fluid container means in sealed fluid communication with the ventilator airway, the connector means having a fluid passageway adapted to be connected in fluid communication with the opening of the fluid container means;

a coupling on said container for coupling said container to said connector; and closure means disposed between the connector fluid passageway and the opening of the fluid container for opening and closing fluid communication between the connector fluid passageway and the opening of the fluid container, the closure means comprising a disc assembly including a first disc fixedly mounted between the connector fluid passageway and the opening of the fluid container and a second disc rotatably mounted to the first disc, the first disc having at least one aperture defined therein, and the second disc having at least one corresponding aperture defined therein.

2. The system of claim 1, wherein the closure means comprises indexing means for switching the closure means between an open position when the fluid container is coupled to the connector means allowing fluid communication between the connector fluid passageway and the opening of the fluid container, and a closed position when the fluid container is removed from the connector means, preventing fluid communication between the connector fluid passageway and the atmosphere.

3. The system of claim 2, wherein the fluid container has a mouth defining said opening in said fluid container, and said indexing means comprises at least one tab disposed on the second, rotatable disc, and at least one corresponding locating stop on the mouth of the fluid container, whereby the second disc can be rotated to the open position by rotation of the fluid container to align the second disc aperture with the first disc aperture to allow fluid communication between the connector means and the fluid container, and whereby the second disc can be rotated to the closed position by rotation of the fluid container bringing the first disc aperture and second disc aperture out of alignment.

4. The system of claim 2 wherein the fluid container has a mouth defining said opening in said fluid container, and said indexing means comprises at least one tab disposed in the mouth of the fluid container, and at least one corresponding locating stop disposed on the second, rotatable disc, whereby the second disc can be rotated to the open position by rotation of the fluid container to align the second disc aperture with the first disc aperture to allow fluid communication between the connector means and the fluid container, and whereby the second disc can be rotated to the closed position by rotation of the fluid container bringing the first disc aperture and second disc aperture out of alignment.

5. A ventilator airway fluid collection system for collecting fluid from a ventilator airway, comprising:

a fluid container for containing fluid from the ventilator airway, the fluid container having an opening through which fluid is received from the ventilator airway;

connector means for connecting the fluid container means in sealed fluid communication with the ventilator airway, the connector means having a fluid passageway adapted to be connected in fluid communication with the opening of the fluid container means;

a coupling on said container for coupling said container to said connector; and closure means disposed between the connector fluid passageway and the opening of the fluid container for opening and closing fluid communication between the connector fluid passageway and the opening of the fluid container, said closure means including indexing means for switching the closure means between an open position when the fluid container is coupled to the connector means allowing fluid communication between the connector fluid passageway and the opening of the fluid container, and a closed position when the fluid container is removed from the connector means, preventing fluid communication between the connector fluid passageway and the atmosphere, the closure means comprising a disc assembly including a first disc fixedly mounted between the connector fluid passageway and the opening of the fluid container and a second disc rotatably mounted to the first disc, the first disc having at least one aperture defined therein, and the second disc having at least one corresponding aperture defined therein.

6. The system of claim 5, wherein the fluid container has a mouth defining said opening in said fluid container, and said indexing means comprises at least one tab disposed on the second, rotatable disc, and at least one corresponding locating stop on the mouth of the fluid container, whereby the second disc can be rotated to the open position by rotation of the fluid container to align the second disc aperture with the first disc aperture to allow fluid communication between the connector means and the fluid container, and whereby the second disc can be rotated to the closed position by rotation of the fluid container bringing the first disc aperture and second disc aperture out of alignment.

7. The system of claim 5, wherein the fluid container has a mouth defining said opening in said fluid container, and said indexing means comprises at least one tab disposed in the mouth of the fluid container, and at least one corresponding locating stop disposed on the second, rotatable disc, whereby the second disc can be rotated to the open position by rotation of the fluid container to align the second disc aperture with the first disc aperture to allow fluid communication between the connector means and the fluid container, and whereby the second disc can be rotated to the closed position by rotation of the fluid container bringing the first disc aperture and second disc aperture out of alignment.

\* \* \* \* \*